US00PP28589P2

(12) United States Plant Patent
Konst

(10) Patent No.: US PP28,589 P2
(45) Date of Patent: Oct. 31, 2017

(54) ***ALSTROEMERIA* PLANT NAMED 'KONCAFIRE'**

(50) Latin Name: *Alstroemeria hybrida*
Varietal Denomination: Koncafire

(71) Applicant: Johannes Wilhelmus Maria Konst, Nieuwveen (NL)

(72) Inventor: Johannes Wilhelmus Maria Konst, Nieuwveen (NL)

(73) Assignee: KONST BREEDING B.V., Nieuwveen (NL)

( * ) Notice: Subject to any disclaimer, the term of this patent is extended or adjusted under 35 U.S.C. 154(b) by 0 days.

(21) Appl. No.: 15/330,210

(22) Filed: Aug. 22, 2016

(51) Int. Cl.
*A01H 5/02* (2006.01)

(52) U.S. Cl.
USPC ..... Plt./309

(58) Field of Classification Search
USPC ..... Plt./309
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Alstroemeria* plant named 'Koncafire', characterized by its compact and mounding plant habit; sturdy and strong plants; vigorous growth habit and rapid growth rate; freely branching habit; numerous bright red-colored flowers with dark purple-colored stripes; and good garden performance.

2 Drawing Sheets

Botanical designation: *Alstroemeria hybrida.*
Cultivar denomination: 'KONCAFIRE'.

BACKGROUND OF THE INVENTION

The present invention relates to a new and distinct cultivar of *Alstroemeria* plant, botanically known as *Alstroemeria hybrida*, typically grown as a container-type garden *Alstroemeria* and hereinafter referred to by the name 'Koncafire'.

The new *Alstroemeria* plant is a product of a planned breeding program conducted by the Inventor in Nieuwveen, The Netherlands. The objective of the breeding program is to create new compact container-type garden *Alstroemeria* plants that have an early and freely flowering habit with attractive leaf and flower coloration.

The new *Alstroemeria* plant originated from a cross-pollination made by the Inventor in Nieuwveen, The Netherlands in September, 2011 of a proprietary selection of *Alstroemeria hybrida* identified as code number 39728-32, not patented, as the female, or seed, parent with *Alstroemeria hybrida* 'Koncalolly', disclosed in U.S. Plant Pat. No. 24,284, as the male, or pollen, parent. The new *Alstroemeria* plant was discovered and selected by the Inventor as a single flowering plant from within the progeny of the stated cross-pollination in a controlled greenhouse environment in Nieuwveen, The Netherlands in June, 2013.

Asexual reproduction of the new *Alstroemeria* plant by in vitro rhizogenesis in a controlled greenhouse environment in Nieuwveen, The Netherlands since October, 2013 has shown that the unique features of this new *Alstroemeria* plant are stable and reproduced true to type in successive generations.

SUMMARY OF THE INVENTION

Plants of the new *Alstroemeria* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Koncafire'. These characteristics in combination distinguish 'Koncafire' as a new and distinct *Alstroemeria* plant:

1. Compact and mounding plant habit.
2. Sturdy and strong plants.
3. Vigorous growth habit and rapid growth rate.
4. Freely branching habit.
5. Numerous bright red flowers with dark purple-colored stripes.
6. Good garden performance.

Plants of the new *Alstroemeria* can be compared to plants of the female parent selection. Plants of the new *Alstroemeria* differ primarily from plants of the female parent selection in the following characteristics:

1. Plants of the new *Alstroemeria* are more compact than plants of the female parent selection.
2. Plants of the new *Alstroemeria* and the female parent selection differ in flower color as flowers of plants of the female parent selection are orange in color.

Plants of the new *Alstroemeria* can be compared to plants of the male parent, 'Koncalolly'. Plants of the new *Alstroemeria* differ primarily from plants of 'Koncalolly' in flower color as plants of 'Koncalolly' have dark red and red purple-colored flowers.

Plants of the new *Alstroemeria* can be compared to plants of the *Alstroemeria hybrida* 'Koncaband', disclosed in U.S. Plant Pat. No. 26,933. In side-by-side comparisons conducted in Nieuwveen, The Netherlands, plants of the new *Alstroemeria* differ from plants of 'Koncaband' in the following characteristics:

1. Plants of the new *Alstroemeria* are shorter and broader than plants of 'Koncaband'.
2. Plants of the new *Alstroemeria* have larger flowers than plants of 'Koncaband'.

3. Plants of the new *Alstroemeria* and 'Koncaband' differ in flower color as plants of 'Koncaband' have lighter red-colored flowers.

BRIEF DESCRIPTION OF THE PHOTOGRAPHS

The accompanying colored photographs illustrate the overall appearance of the new *Alstroemeria* plant showing the colors as true as it is reasonably possible to obtain in colored reproductions of this type. Colors in the photographs may differ slightly from the color values cited in the detailed botanical description which accurately describe the colors of the new *Alstroemeria* plant.

The photograph on the first sheet is a side perspective view of a typical flowering plant of 'Koncafire' grown in container.

The photograph on the second sheet is a close-up view of a typical flower of 'Koncafire'.

DETAILED BOTANICAL DESCRIPTION

The aforementioned photographs and following observations and measurements describe plants of the new *Alstroemeria* grown during the late spring in 19-cm containers in a glass-covered greenhouse in Nieuwveen, The Netherlands and under cultural practices typical of commercial container-type *Alstroemeria* production. During the production of the plants, day temperatures ranged from 6° C. to 30° C. and night temperatures ranged from 6° C. to 20° C. Plants were 36 weeks old when the photographs and description were taken. In the following description, color references are made to The Royal Horticultural Society Colour Chart, 2015 Edition, except where general terms of ordinary dictionary significance are used.

Botanical classification: *Alstroemeria hybrida* 'Koncafire'.

Parentage:

*Female, or seed, parent*.—Proprietary selection of *Alstroemeria hybrida* identified as code number 39728-32, not patented.

*Male or pollen parent*.—*Alstroemeria hybrida* 'Koncalolly', disclosed in U.S. Plant Pat. No. 24,284.

Propagation:

*Type*.—In vitro rhizogenesis.

*Root description*.—Thick, fleshy; typically white in color, actual color of the roots is dependent on substrate composition, water quality, fertilizers, substrate temperature and physiological age of roots.

*Rooting habit*.—Freely branching; dense.

*Rhizome description*.—Shape: Elongate; rounded. Length: About 7 cm. Diameter: About 1.3 cm. Texture: Smooth. Color: Close to 161D.

Plant description:

*Plant and growth habit*.—Perennial garden plant; compact and mounded; freely branching habit, bushy appearance; sturdy and strong plants; vigorous growth habit; rapid growth rate.

*Plant height*.—About 28 cm.

*Plant diameter* (*area of spread*).—About 45 cm.

Stem description:

*Aspect*.—Mostly upright.

*Internode length*.—About 4 mm to 12 mm.

*Strength*.—Strong, sturdy.

*Texture*.—Smooth, glabrous.

*Color*.—Close to 138A.

Leaf description:

*Arrangement*.—Alternate; below the peduncle, arranged in a single whorl; leaves sessile.

*Length*.—About 4.2 cm to 9.6 cm.

*Width*.—About 1.1 cm to 2.5 cm.

*Shape*.—Lanceolate.

*Apex*.—Acute.

*Base*.—Attenuate.

*Margin*.—Entire.

*Texture and luster, upper and lower surfaces*.—Smooth, glabrous; slightly glossy.

*Venation pattern*.—Parallel.

*Color*.—Developing leaves, upper surface: Close to 138A. Developing leaves, lower surface: Close to 137C. Fully expanded leaves, upper surface: Close to 137B; venation, close to 137D. Fully expanded leaves, lower surface: Close to 137C; venation, close to 138B.

Flower description:

*Flower type and habit*.—Single cup-shaped flowers arranged in compound umbels; flowers face upright to outwardly; freely flowering habit with up to 16 flowers developing per inflorescence and about 40 to 75 flowers developing per plant during the flowering season.

*Natural flowering season*.—Flowering continuous from the late spring until the autumn in The Netherlands; early-flowering habit, plants begin flowering about 6 to 16 weeks after stem initiation.

*Fragrance*.—None detected.

*Flower longevity on the plant*.—About one to three weeks, longevity is temperature-dependent; flowers not persistent.

*Flower longevity as a cut flower*.—About one to two weeks, longevity is temperature-dependent; flowers not persistent.

*Flower buds*.—Length: About 4.5 cm. Diameter: About 1.6 cm. Shape: Ovoid. Color: Close to N45A; at the apex, close to 146C.

*Umbel height*.—About 11 cm.

*Umbel diameter*.—About 19 cm.

*Flower diameter*.—About 6.5 cm.

*Flower depth* (*height*).—About 7 cm.

*Perianth*.—Arrangement: Six arranged in two whorls, each whorl with two lateral and one median segments. Size, inner perianth: Length, lateral segments: About 6 cm. Width, lateral segments: About 2.1 cm. Length, median segment: About 5 cm. Width, median segment: About 1.9 cm. Size, outer perianth: Length, lateral segments: About 6.5 cm. Width, lateral segments: About 3.4 cm. Length, median segment: About 6.8 cm. Width, median segment: About 3.4 cm. Shape, inner perianth, lateral and median segments: Oblanceolate. Shape, outer perianth, lateral and median segments: Obovate. Apex, inner perianth, lateral and median segments: Acute. Apex, outer perianth, lateral and median segments: Emarginate, wishbone-shaped. Base, inner and outer perianths, lateral and median segments: Attenuate. Margin, inner and outer perianths, lateral and median segments: Proximally, entire; distally, finely dentate. Texture, inner and outer perianths, lateral and median segments: Smooth, glabrous. Luster, inner and outer perianths, lateral and median segments: Matte, dull. Color, inner perianth, lateral segments: When opening, upper surface: Towards the apex, close to 42A; mid-section, close to 18C; towards the base, close to 47D; stripes, close to 187A. When opening, lower surface: Towards the apex, close to 42B; mid-section, close to 41D; towards the base, close to 42D; stripes, close to 187A. Fully opened, upper surface: Towards the apex, close to 45A; mid-section, close to 16A; towards the base, close to 49A; stripes, close to 187A; color does not change with development. Fully opened, lower surface: Towards the apex, close to 42B; mid-section, close to 33C; towards the base, close to 34A; stripes, close to 187A. Color, inner perianth, median segment: When opening, upper surface: Towards the apex, close to 42A; towards the base, close to 155C; stripes, close to 187A. When opening, lower surface: Towards the apex, close to 42A; mid-section, close to 42B; towards the base, close to 41D; stripes, close to 187A. Fully opened, upper surface: Towards the apex, close to 45A; mid-section, close to 39B; towards the base, close to 38C; stripes, close to 187A; color does not change with development. Fully opened, lower surface: Towards the apex, close to 44A; mid-section, close to 42B; towards the base, close to 41C; stripes, close to 187A. Color, outer perianth, lateral segments: When opening, upper surface: Close to 45A. When opening, lower surface: Close to N45D. Fully opened, upper surface: Close to N45C; color does not change with development. Fully opened, lower surface: Close to 45A; venation, close to 153B. Color, outer perianth, median segment: When opening, upper surface: Close to N45B; towards the base, close to N45D. When opening, lower surface: Close to N45C; towards the base, close to N45D. Fully opened, upper surface: Close to N45C; color does not change with development. Fully opened, lower surface: Close to 45A; venation, close to 153B.

*Pedicels*.—Length: About 1.5 cm to 2.2 cm. Diameter: About 3 mm. Strength: Strong. Angle: About 45° to 70° from vertical. Texture: Smooth, glabrous. Color, upper and lower surfaces: Close to 137C.

*Reproductive organs*.—Stamens: Quantity per flower: Six. Anther shape: Oval. Anther size: About 3 mm by 8 mm. Anther color: Close to 164A. Pollen amount: Abundant. Pollen color: Close to 163B. Pistils: Quantity per flower: One. Pistil length: About 4.8 cm. Style length: About 4.3 cm. Style color: Close to 45C. Stigma color: Close to 46A. Ovary color: Close to 137C.

*Fruits and seeds*.—Fruit and seed development has not been observed on plants of the new *Alstroemeria*.

Disease & pest resistance: Plants of the new *Alstroemeria* have not been observed to be resistant to pathogens and pests common to *Alstroemeria* plants.

Garden performance: Plants of the new *Alstroemeria* have been observed to have good garden performance and to tolerate wind, rain and temperatures ranging from about 6° C. to about 35° C.

It is claimed:

1. A new and distinct *Alstroemeria* plant named 'Koncafire' as illustrated and described.

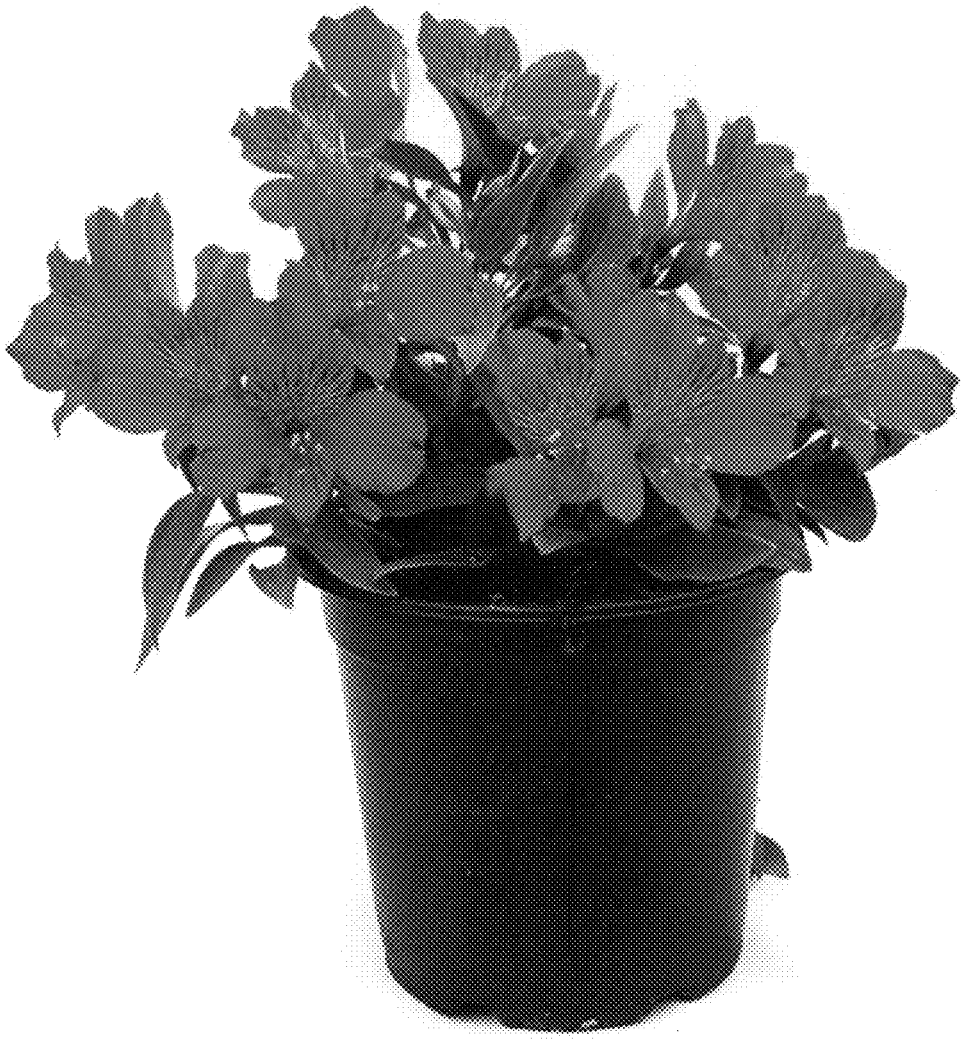

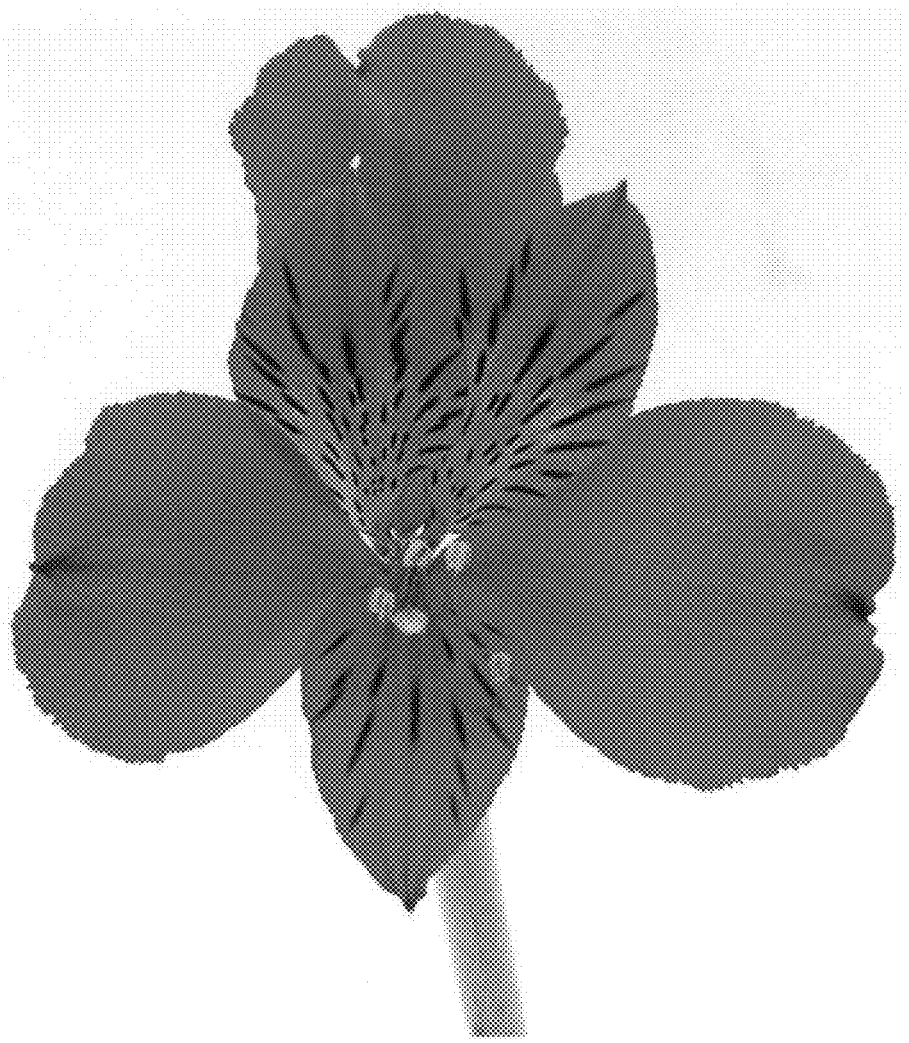

* * * * *